US012712167B2

(12) United States Patent
Fournier et al.

(10) Patent No.: US 12,712,167 B2
(45) Date of Patent: Aug. 18, 2026

(54) SYSTEM AND METHOD FOR ANALYSING VOLATILE ORGANIC COMPOUNDS (VOC) BY LOW-TEMPERATURE PLASMA AND MASS SPECTROMETRY (LTP-MS)

(71) Applicants: UNIVERSITE DE LILLE, Lille (FR); INSERM (INSTITUT NATIONAL DE LA SANTÉ ET DE LA RECHERCHE MÉDICALE), Paris (FR); CENTRE HOSPITALIER REGIONAL ET UNIVERSITAIRE DE LILLE (CHRU), Lille (FR)

(72) Inventors: Isabelle Fournier, Bourghelles (FR); Julien Franck, Fretin (FR); Michel Salzet, Bourghelles (FR); Flore Herve, Semblançay (FR)

(73) Assignees: UNIVERSITE DE LILLE, Lille (FR); INSERM (INSTITUT NATIONAL DE LA SANTÉ ET DE LA RECHERCHE MÉDICALE), Paris (FR); CENTRE HOSPITALIER REGIONAL ET UNIVERSITAIRE DE LILLE (CHRU), Lille (FR)

( * ) Notice: Subject to any disclaimer, the term of this patent is extended or adjusted under 35 U.S.C. 154(b) by 685 days.

(21) Appl. No.: 17/926,730

(22) PCT Filed: May 20, 2021

(86) PCT No.: PCT/FR2021/050923

§ 371 (c)(1),
(2) Date: Nov. 21, 2022

(87) PCT Pub. No.: WO2021/234319

PCT Pub. Date: Nov. 25, 2021

(65) Prior Publication Data

US 2023/0207300 A1 Jun. 29, 2023

(30) Foreign Application Priority Data

May 20, 2020 (FR) ...................................... 2005155

(51) Int. Cl.
*H01J 49/04* (2006.01)
*G01N 33/497* (2006.01)
(Continued)

(52) U.S. Cl.
CPC .......... *H01J 49/049* (2013.01); *G01N 33/497* (2013.01); *H01J 49/105* (2013.01); *H01J 49/26* (2013.01)

(58) Field of Classification Search
CPC .. A61B 5/082; A61B 5/4312; G01N 2560/00; G01N 33/497; G01N 33/57415;
(Continued)

(56) References Cited

U.S. PATENT DOCUMENTS

2010/0019140 A1* 1/2010 Amirav ................ H01J 49/049 250/288
2011/0031392 A1* 2/2011 McEwen .............. H01J 49/107 250/288
(Continued)

OTHER PUBLICATIONS

International Search Report issued on Nov. 4, 2021, in corresponding International Application No. PCT/FR2021/050923; 11 pages (including English translation).
(Continued)

*Primary Examiner* — Jennifer Wecker
(74) *Attorney, Agent, or Firm* — Maier & Maier, PLLC

(57) ABSTRACT

A system and method for analyzing volatile organic compounds (VOCs) adsorbed on an adsorbent membrane, by low-temperature plasma and mass spectrometry (LTP-MS). The system includes a receptacle for receiving the adsorbent membrane, a low-temperature plasma ionizer configured to emit a plasma stream in a plasma emission direction, thereby
(Continued)

ionizing the VOCs adsorbed by the membrane and forming a VOC-laden ionized gas, and a mass spectrometer for analyzing the ionized VOCs.

17 Claims, 8 Drawing Sheets

(51) Int. Cl.
*H01J 49/10* (2006.01)
*H01J 49/26* (2006.01)

(58) Field of Classification Search
CPC ........ H01J 49/049; H01J 49/105; H01J 49/14; H01J 49/26
See application file for complete search history.

(56) References Cited

U.S. PATENT DOCUMENTS

2015/0144777 A1 5/2015 Shiea et al.
2015/0235829 A1* 8/2015 Chung ................ H01J 49/0031 250/288
2018/0038838 A1* 2/2018 Karancsi ................ G01N 33/92

OTHER PUBLICATIONS

Mulligan et al., "Fast analysis of high-energy compounds and agricultural chemicals in water with desorption electrospray ionization mass spectrometry", Rapid Communications in Mass Spectrometry, GB, vol. 21, No. 22, Oct. 25, 2007, 9 pages.
Harper et al., "Low-Temperature Plasma Probe for Ambient Desorption Ionization", Analytical Chemistry, American Chemical Society, vol. 80, No. 23, Dec. 1, 2008, 8 pages.
Matz et al., "On-line gas chromatography-mass spectrometry for process monitoring using solvent-free sample preparation", Journal of Chromatography A, Elsevier, Amsterdam, NL, vol. 819, No. 1-2, Sep. 11, 1998, 10 pages.
Bruheim et al., "Thin-Film Microextraction" Analytical Chemistry, American Chemical Society, vol. 75, No. 4, Feb. 15, 2003, 9 pages.
Reyes-Garces et al., "Advances in Solid Phase Microextraction and Perspective on Future Directions", Analytical Chemistry, vol. 90, No. 1, Nov. 8, 2018, 59 pages.
Deng et al., "Strategies for coupling solid-phase microextraction with mass spectrometry", TRAC Trends in Analytical Chemistry, Amsterdam, NL, vol. 55, Jan. 7, 2014, 13 pages.
Almasian et al., "Development of a graphite low-temperature plasma source with dual-mode in-source fragmentation for ambient mass spectrometry : Graphite LTP source for ambient mass spectrometry" Rapid Communications in Mass Spectrometry, GB, vol. 24, No. 6, Feb. 18, 2010, 7 pages.

* cited by examiner

P1
P2
S1
S2
TOF MS ES+

SYSTEM AND METHOD FOR ANALYSING VOLATILE ORGANIC COMPOUNDS (VOC) BY LOW-TEMPERATURE PLASMA AND MASS SPECTROMETRY (LTP-MS)

FIELD

This disclosure relates to the field of detecting volatile organic compounds (VOCs). In particular, this disclosure relates to the field of systems for analyzing VOCs, and more particularly VOCs adsorbed on an adsorbent membrane, as well as methods for analyzing such VOCs.

BACKGROUND

Several strategies are commonly used for diagnosis based on VOC analysis. Some rely, for example, on mass spectrometry (MS) methods. However, these methods do not allow real-time and in vivo analysis. The most commonly used techniques for VOC analysis are presented below. In addition, most diagnoses are based on the analysis of exhaled air.

Thus, among these methods, the techniques coupling gas chromatography and mass spectrometry (GC-MS) or flame ionization detection (gas chromatography-FID) are considered by the U.S. Environmental Protection Agency (EPA, https://www.epa.gov) as the benchmark for VOC analysis. However, they do not allow direct real-time analysis such as the analysis of exhaled air and ambient air and require preconcentrating the samples on resins or adsorbent stationary phases. The samples are then desorbed at high temperature (from 200° C. to 300° C.) then introduced into the GC column, thereby enabling their separation and then their on-line detection by MS or FID. Even so, these techniques still remain the ones providing the most information in terms of identification and quantification. However, they have the disadvantage of requiring a long analysis time of about 30 min. Furthermore, FIDs are only sensitive to carbon compounds and provide little qualitative information, and do not allow identification.

There is also selected-ion flow-tube mass spectrometry (SIFT-MS). This technique was developed in the 1970s and allows on-line and real-time analysis of traces of VOCs from gaseous samples (e.g. exhaled air) or biological fluids such as urine and blood, using what is referred to as the headspace method. It is based on the production of primary ions in a plasma source, from air and water vapor. From this plasma, a single species of ions is selected using a quadrupole, such as the ions $H_3O^+$, $NO^+$, and $O_2^+$, which are injected into a cell in order to ionize the present VOCs, for their analysis according to their mass-to-charge ratio (m/z) in a second quadrupole. The ionization being soft, this mainly leads to the formation of molecular ions, thus simplifying the interpretation of the mass spectra, particularly in the case of complex mixtures such as exhaled air. This technique makes it possible to independently select three primary ions which allow obtaining three different mass spectra; this is of interest for the analysis of compounds with different properties. In addition, SIFT-MS allows real-time analysis and simultaneous quantification of multiple VOCs without prior pretreatment. It is therefore fast, easy to manipulate, and offers a detection limit that is on the order of one ppb. However, it has the disadvantage of exclusively analyzing gaseous samples and does not allow surface analysis.

Another known technique is proton transfer mass spectrometry (PTR-MS). This technique was developed in the mid-1990s, is an evolution of SIFT, and is based on the gas phase proton transfer reaction between hydronium ions ($H_3O^+$) and VOCs. The proton transfer reaction takes place in a drift cell which allows limiting the formation of clusters with the water molecules contained in ambient air. As the exothermicity of the proton transfer is weak, little or no fragmentation is observed which allows detecting intact species, thus simplifying the identification of VOCs. Originally, PRT-MS was equipped with a quadrupole as the analyzer, but other instruments such as ion trap or time of flight (TOF) analyzers were integrated into PTR-MS. In the 2000s, the introduction of TOF made it possible to detect VOCs with greater resolution and also greater accuracy in the mass measurement. PTR-MS has a detection limit on the order of one ppt and above all does not require preconcentration of the sample which can be time-consuming. In addition, the advantage of this technique lies in its almost real-time analysis without the need to adsorb and then desorb the sample, such adsorption and desorption possibly resulting in losses related to the properties of the substrate. Since PTR-MS is a VOC analysis technique that is fast and easy to manipulate, the number of samples that can be studied is significantly higher than with gas chromatography-mass spectrometry (GC-MS), although the amount of information remains lower. However, like SIFT-MS, this technique only allows analysis of gaseous samples and does not allow analysis of surfaces. Moreover, as this technique based on proton transfer, it is limited to analytes having a greater proton affinity than that of the hydronium ion $H_3O^+$.

There is also membrane introduction mass spectrometry (MIMS). This technique was introduced in 1963 and allows direct and continuous analysis of VOCs comprised in a complex mixture. MIMS is based on the use of semi-permeable membranes, such as polydimethylsiloxane (PDMS) (or silicone) membranes, as an interface between the sample and the mass spectrometer. The membrane allows preconcentration of the VOCs according to their physicochemical properties, and their transfer into the mass spectrometer, while simultaneously eliminating the rest of the unretained sample. Adsorbed VOCs diffuse through the membrane and are evaporated directly into the ion source. Consequently, the ion suppression phenomena related to the matrix of the sample are greatly reduced. The direct coupling between the semi-permeable membranes and the mass spectrometer makes it possible to obtain a method of fast continuous analysis with a minimum of sample preparation. The selectivity and sensitivity of this technique are governed by the ionization efficiency and the mass spectrometer but also by the selectivity of the membranes used. This technique is applicable to liquid or gaseous samples.

Finally, the technique combining low-temperature plasma and mass spectrometry (LTP-MS) was introduced in 1996. A plasma is generated using dielectric barrier discharge (DBD) obtained by the application of high voltage and the use of a gas such as helium. This plasma allows ionization of the VOCs directly on the surface of solid or liquid samples, but also of the VOCs already present in gaseous phase (ambient air and exhaled breath). LTP is a source of soft ionization enabling real-time analysis of VOCs from solid, liquid, or gaseous samples, and possibly directly on the surface thereof. This technique is also compatible with the analysis of exhaled air and ambient air.

SUMMARY

The present disclosure improves the situation.

Thus, the present invention proposes a system for analyzing VOCs adsorbed on an adsorbent membrane, by LTP-MS, comprising:

- a receptacle for receiving the adsorbent membrane;
- a low-temperature plasma ionizer suitable for emitting a plasma stream in a plasma emission direction, thus ionizing the VOCs adsorbed by the membrane and forming an ionized gas laden with VOCs; and
- a mass spectrometer to analyze the ionized VOCs.

Another aspect of the invention is a method for analyzing VOCs adsorbed on an adsorbent membrane, by LTP-MS, comprising:

- providing an adsorbent membrane on which VOCs have been adsorbed;
- desorption the VOCs adsorbed on the adsorbent membrane;
- low-temperature plasma ionizing the desorbed VOCs, thus forming an ionized gas; and
- analyzing of the ionized gas, by mass spectrometry.

Another aspect of the invention is a method for diagnostic aid, in particular for breast cancer, comprising the method described above, in which VOCs from the patient have been adsorbed on the adsorbent membrane, the method further comprising determining the medical status of the patient based on the results of the comparison.

BRIEF DESCRIPTION OF DRAWINGS

Other features, details, and advantages will become apparent upon reading the detailed description below, and upon analyzing the appended drawings, in which:

FIG. 11 is a graph illustrating the minimum size (in ångströms) of the pores of an adsorbent membrane to allow a molecule of a given size (in daltons) to pass through.

DETAILED DESCRIPTION

Figure 1:
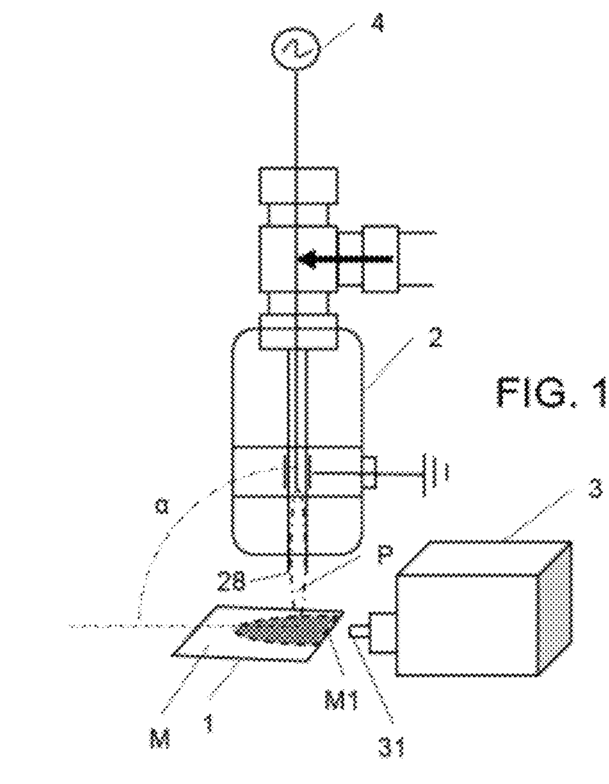
FIG. 1 shows a diagram of a first system where desorption and ionization are carried out at the same location or in close proximity.

The drawings and the description below for the most part contain elements that are certain in nature. Therefore not only can they serve to provide a better understanding of this disclosure, but where appropriate they also contribute to its definition.

System

With reference to the drawings, a system for analyzing VOCs adsorbed on an adsorbent membrane, by LTP-MS, will be described below. Such a system, which may be transportable, comprises a receptacle 1 for receiving the adsorbent membrane M, a low-temperature plasma ionizer 2 (LTP ionizer) designed to emit a plasma stream P in a plasma emission direction thus ionizing the VOCs adsorbed by the membrane M, and a mass spectrometer (MS) 3 configured for analyzing the gas mixture comprising ionized VOCs such as cyclohexanol $C_6H_{11}$—OH, dodecan-2-one $CH_3$—CO—$(CH_2)_9$—$CH_3$, nonan-2-one $CH_3$—CO—$(CH_2)_6$—$CH_3$, and 4-methylheptan-2-one $CH_3$—CO—$CH_2$—CH$(CH_3)$—$(CH_2)_2$—$CH_3$. These VOCs are present in particular in samples taken from patients suffering from breast cancer. The system may further comprise an ion mobility cell (not shown in the figures) for LTP-IMS-MS analysis (IMS for ion mobility spectrometry). This ion mobility cell may be provided separately from the MS between the latter and the LTP ionizer, or may be an integral part of the MS.

Throughout this description, reference is made to ionized species, such as ionized gas or ionized VOCs. Of course, this does not necessarily mean that all the molecules of the ionized species have been ionized by the plasma, but that at least some of the gas or VOCs have been ionized.

The system may further comprise a power supply 4 for powering the LTP ionizer 2, in particular at a voltage of between 1 and 30 kV (preferably 7 to 18 kV) and/or at a frequency of between 0.8 and 30 kHz (preferably 2 to 10 kHz). Combining the preferred ranges is particularly suitable for one of the many contemplated applications: detection of breast cancer. The power may be direct current or alternating current. In the latter case, the following combinations are of particular interest: (4 kV; 24 kHz) to (6 kV; 20 kHz); (5.5 kV; 25 kHz) to (7 kV; 21 kHz); (6.5 kV, 25 kHz) to (10 kV; 23.5 kHz). The ionizer may be configured to produce plasma continuously or in pulses.

Figure 9:
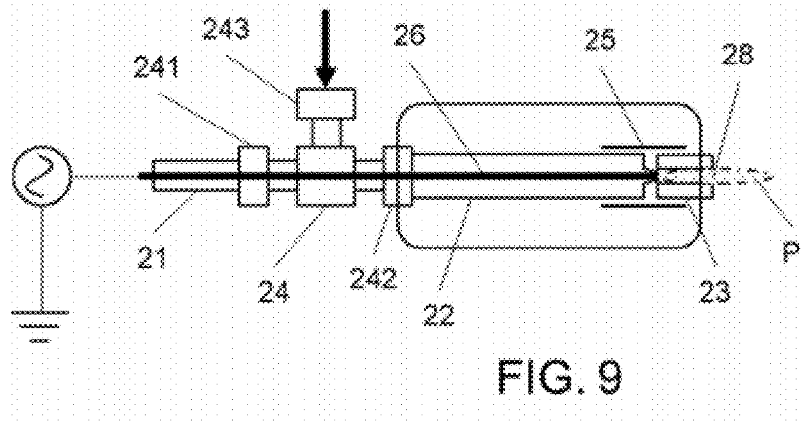
FIG. 9 shows a diagram of an LTP ionizer with one electrode.
Figure 10:
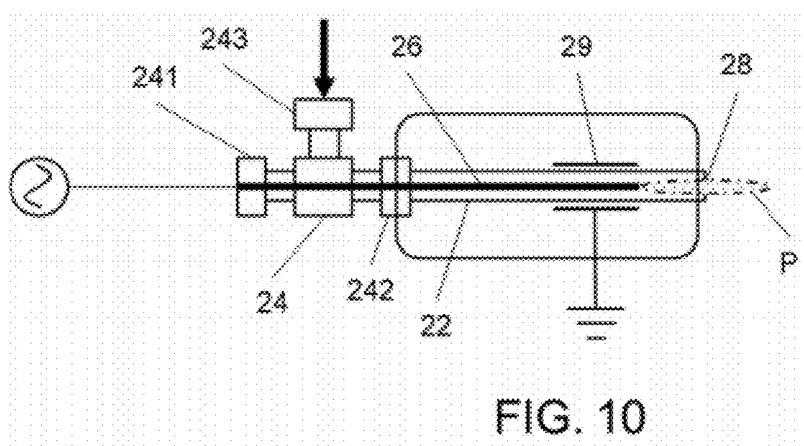
FIG. 10 shows a schematic of an LTP ionizer with two electrodes.

The LTP ionizer 2 may be of two types: a first type with one electrode (FIG. 9) and a second type with two electrodes (FIG. 10). In the figures representing the system, only the LTP ionizer 2 with two electrodes is shown, but this can be replaced by an LTP ionizer 2 with one electrode.

Regardless of the type, the LTP ionizer 2 typically comprises a T-connector 24 with two coaxial arms 241, 242 and a transverse arm 243, a dielectric barrier 22 connected to one of the two coaxial arms, an electrode extending through the T-connector 24 via the two coaxial arms 241, 242 and the dielectric barrier 22 to a position close to and upstream of the plasma outlet 28. The electrode 26 may be connected to the power supply 4 during operation. The electrode 26 may be made of copper. Preferably, the electrode 26 is a metal wire, for example 1.5 mm in diameter.

The inert gas of the LTP, for which the transverse arm 243 of the T-connector 24 serves as the injection inlet, may be dinitrogen, water vapor, or a noble gas. In the case where the inert gas is a noble gas, this noble gas may be argon, helium, or neon. A mixture of these mentioned gases is also possible. The LTP ionizer 2 may be configured to inject inert gas at a flow rate of between 50 and 1000 mL/min.

The LTP ionizer 2 with one electrode (FIG. 9) typically further comprises three glass tubes 21, 22, 23 connected end to end: i.e. the second tube 22 is connected by one of its ends to the first tube 21 and by the other of its ends to the third tube 23. It also comprises a flexible tube 25. The two coaxial arms 241, 242 of the T-connector 24 connect the first tube 21 to the second tube 22. The flexible tube 25 connects the second tube 22 and the third tube 23. The electrode 26 extends inside the first and second tubes 21, 22, in particular from the end of the first tube 21 not connected to the second tube 22, to the end of the second tube 22 connected to the third tube 23, without extending beyond the second tube 22. The second tube 22 forms the barrier for the dielectric barrier discharge and the third tube 23 forms a capillary extension.

The LTP ionizer 2 with two electrodes (FIG. 10) typically further comprises a glass tube 22 forming the dielectric barrier and extending through the T-connector 24 from the first coaxial arm 241 thereof, to the plasma outlet 28 formed by one end of the glass tube 22. The first electrode 26 extends through the glass tube 22 to a position downstream of the plasma outlet 28. The LTP ionizer 2 comprises a second electrode 29 placed around the second tube 22 so as to also surround the first electrode 26 and not extend beyond the end thereof. The second electrode 29 thus has an annular shape. The second electrode 29 is preferably made of copper and grounded to serve as a reference electrode.

This disclosure also encompasses LTP ionizers 2 having the same structure as the ionizer with one electrode described above but with two electrodes, the second electrode serving as reference; as well as LTP ionizers 2 having the same structure as the ionizer with two electrodes described above but with one electrode, the ground of the power supply serving as reference.

Figure 2:
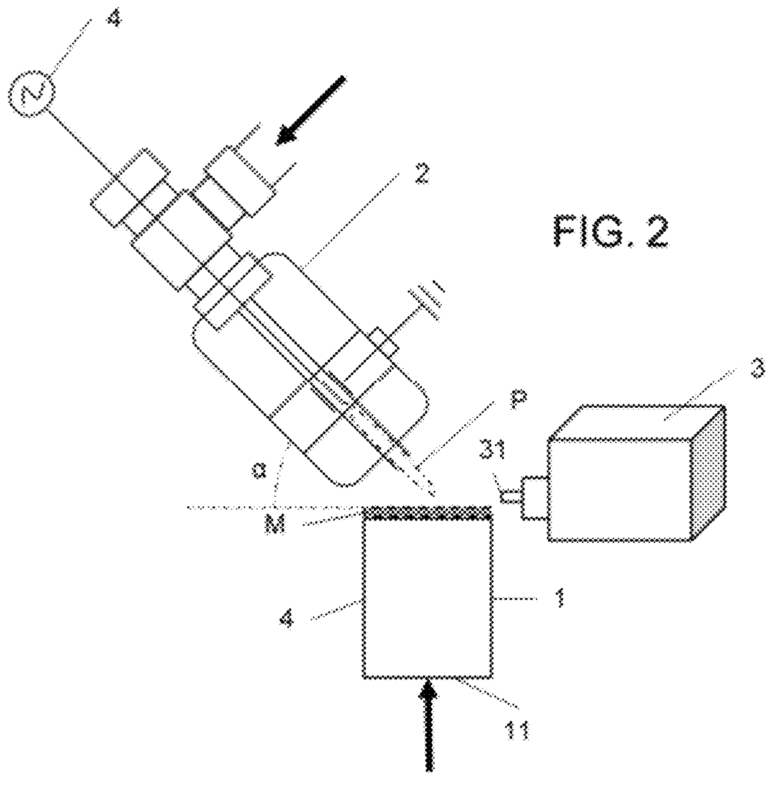
FIG. 2 shows a diagram of a second system where desorption and ionization are carried out at the same location or in close proximity.
Figure 3:
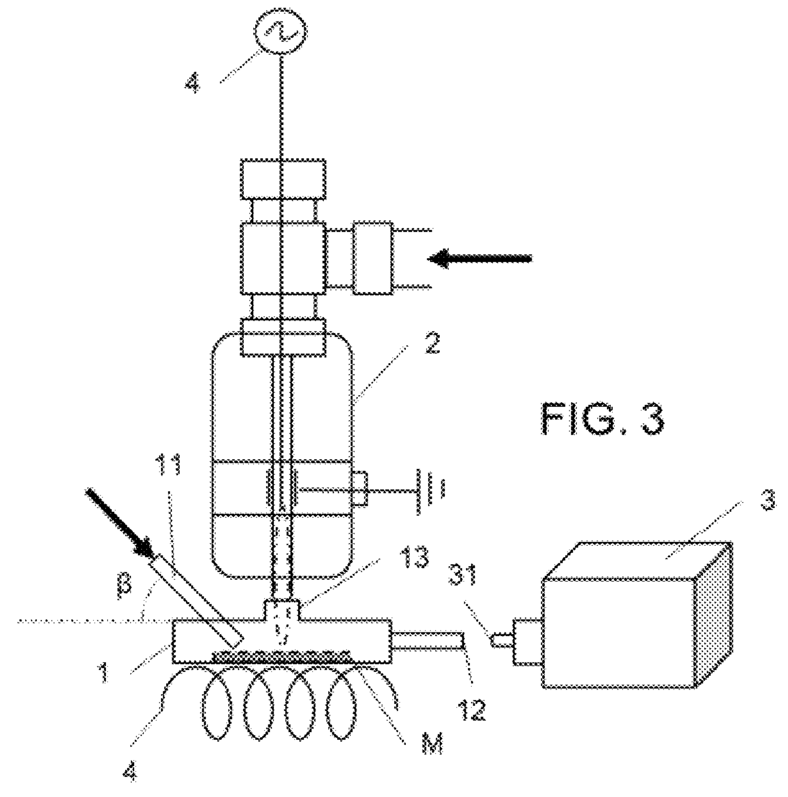
FIG. 3 shows a diagram of a third system where desorption and ionization are carried out at the same location or in close proximity.
Figure 4:
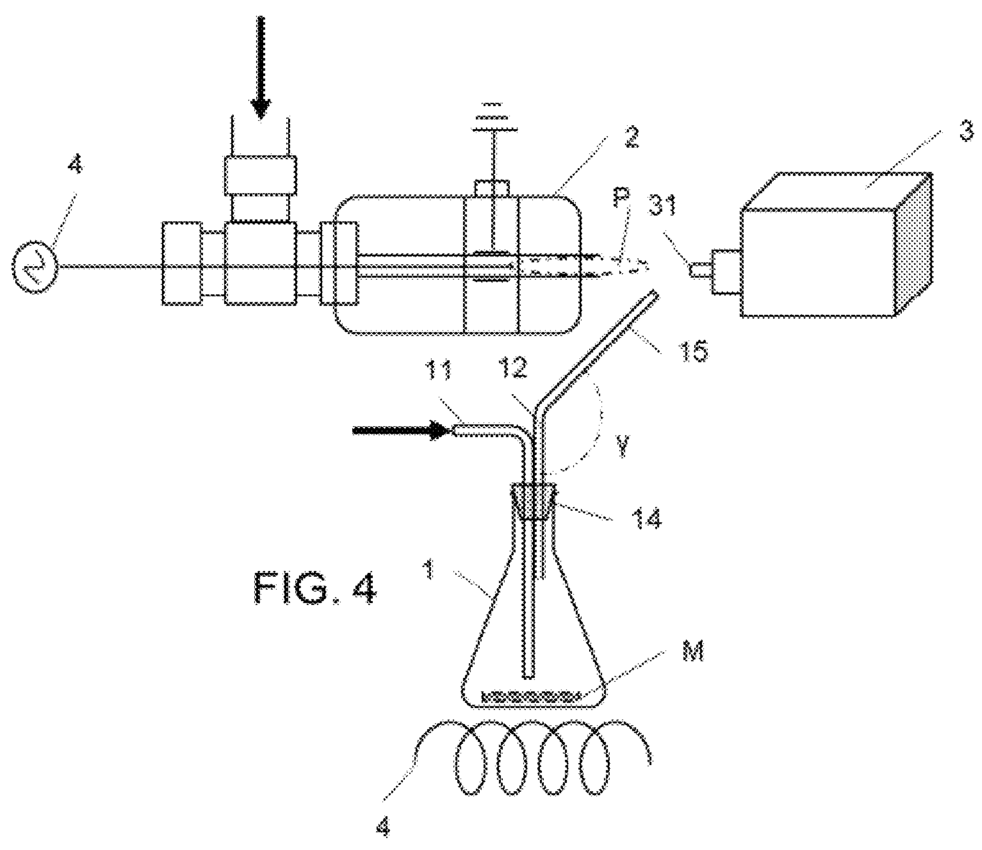
FIG. 4 shows a diagram of a first system where desorption and ionization are carried out remotely.
Figure 5:
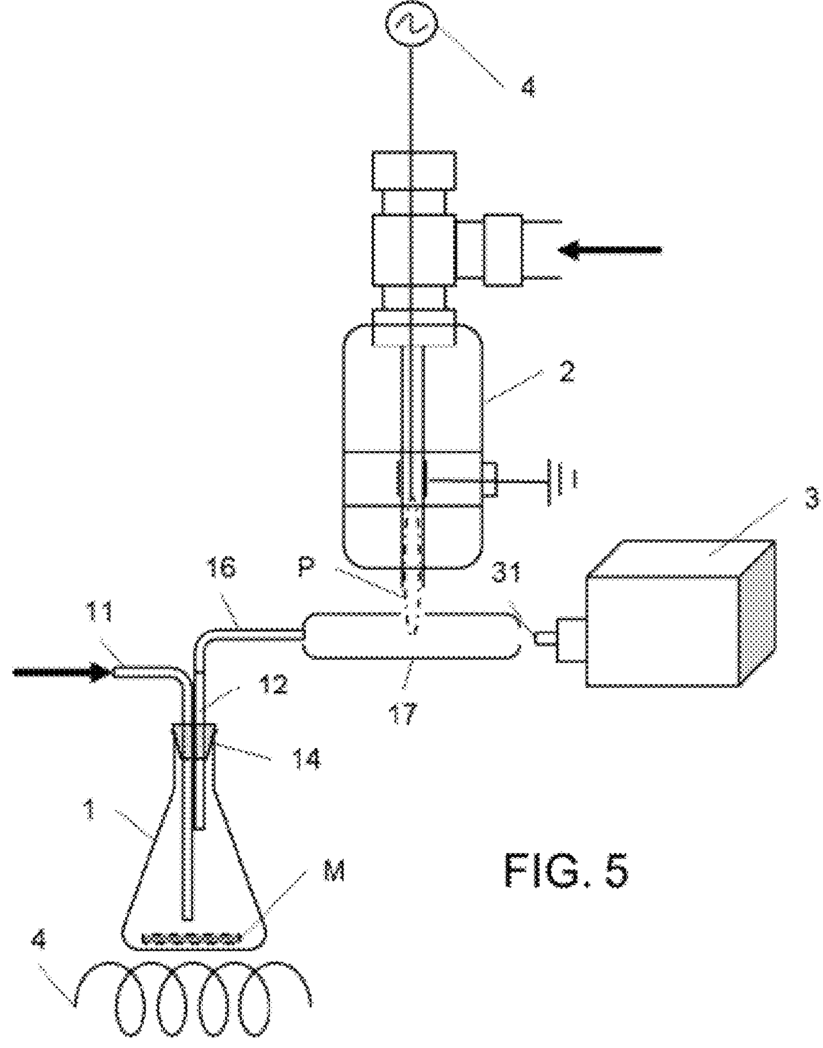
FIG. 5 shows a diagram of a second system where desorption and ionization are carried out remotely.

Two embodiments are possible. These two embodiments differ from each other by the location of the ionization, which may be at the VOC desorption site or remotely from it. FIGS. 1 to 3 show variants in which the ionization is carried out at the location of or at the very least close to the desorption site of the VOCs, and FIGS. 4 to 5 illustrate variants in which the ionization is carried out remotely from the desorption site of the VOCs.

Thus, FIGS. 1 to 3 show systems in which the receptacle 1 is placed under the plasma flow P so that the plasma flow P is directed towards the membrane M when the latter is received in the receptacle 1. In this embodiment, the receptacle 1 and the LTP ionizer 2 are arranged so that the plasma plume P touches or is flush with the upper surface of the membrane M when the membrane is positioned on the receptacle 1. Still in this embodiment, a heater 4 (preferably homogeneous) may further be provided in the system to heat the membrane M and thus help desorb the VOCs. Typically, this heater 4 is provided below the receptacle 1 which transmits the heat generated by the heater 4 to the membrane M. The heater 4 is configured to allow heating of between 0 and 500° C. (preferably between 0 and 400° C., in particular between 20° and 300° C. or even between 225 and 275° C.; for example 50° C., 100° C., 150° C., 200° C., 250° C., 300° C., 350° C., 400° C., 450° C.) and to assist with desorption of the VOCs.

More particularly, FIG. 1 shows a system in which the receptacle 1 is arranged immediately below the LTP ionizer 2 and close to the inlet 31 of the MS 3. Thus, the receptacle 1 is arranged so that the formed plasma plume P is directed towards the adsorbent membrane M. For example, the receptacle 1 may be arranged so that a front edge M1 of the adsorbent membrane M, when the latter is received by the receptacle, is located between 0 and 20 mm from the inlet 31 of the MS. Additionally or alternatively, the receptacle 1 and the LTP ionizer 2 may be arranged so that the outlet 28 of the plasma plume and the surface of the adsorbent membrane M, when the latter is in place, are spaced apart by 0 to 20 mm. The LTP ionizer 2 may also be arranged to rotate so that the angle α formed by the plasma plume P and the surface of the adsorbent membrane, when the latter is in place, is between 0 and 90°, preferably between 35 and 75°, thus making it possible to force the gas in the direction of the MS. The axis of rotation, being horizontal, is perpendicular to the axis of the inlet 31 of the MS; the angle α being acute when the LTP ionizer 2 is remote from the MS 3. Thus, in this variant of the first embodiment, the plasma plume P generated by the LTP ionizer 2 has two functions: desorbing the VOCs and ionizing them.

FIG. 2 shows a system similar to the one in FIG. 1. The difference lies in the receptacle 1 comprising a carrier gas inlet 11 on a lower surface of the receptacle. A carrier gas can thus be injected under the lower surface of the adsorbent membrane M. The carrier gas may in particular be an inert gas, for example dinitrogen, helium, argon, or a mixture thereof. Preferably, the cross-section of the carrier gas inlet 11 has substantially the same dimensions as the membrane M. For the membrane M to be supported, a grid is provided at the carrier gas inlet. The gas source is preferably suitable for emitting a carrier gas flow of between 0.5 and 7 L/min. The gas source may be the same as the one for the MS; above 7 L/min, there is a risk of disrupting the plasma. This carrier gas inlet may be extended by an injection tube connected to a carrier gas source. Preferably, heating is provided around the injection tube.

FIG. 3 shows a system in which the receptacle 1 is a container that is resealable so as to form a sealed environment except for a gas inlet and gas outlet as well as a plasma inlet. The container 1 is therefore closed and can be hermetically sealed. The container thus comprises a carrier gas inlet 11 for the entry of a carrier gas into the container 1, a plasma inlet 13, and a gas outlet 12 for the exit of an ionized gas laden with VOCs comprising the carrier gas and potentially ionized VOCs. The carrier gas may in particular be an inert gas, for example dinitrogen, helium, argon, or a mixture thereof.

The container 1 may have a cylindrical geometry with a lower support surface and an upper surface which are parallel to each other, and a side surface connecting the lower and upper surfaces.

Furthermore, the gas inlet 11 may be an injection tube connected at its free end to a source of inert gas. The axis of the injection tube and the upper surface of the container may form an angle β of between 30 and 750 or even between 35 and 75°, making it possible to force the gas towards the gas outlet 12. The inside diameter of the injection tube may be between 2 and 10 mm. The gas source is preferably suitable for emitting a flow rate of inert gas of between 0.5 and 7 L/min. The gas source may be the same as for the MS; above 7 L/min, there is a risk of disrupting the plasma The plasma inlet 13 may be an orifice created in the upper surface of the container 1. Alternatively, the plasma inlet 13 may be a short tube extending from the upper surface of the container 1. In either case, the plasma inlet 13 can be connected to the plasma outlet orifice of the LTP ionizer.

This connection may be direct, with the plasma outlet orifice of the LTP ionizer in contact with the plasma inlet 13, or via a connector (not shown). This connection may be hermetic or non-hermetic.

The outlet 12 may be a guide tube for guiding ionized gas to the inlet 31 of the MS. It is preferably created in a side surface of the container 1. The axis of the guide tube is preferably horizontal and connects the outlet of the container 1 and the inlet 31 of the MS. The inside diameter of the guide tube may be between 2 and 12 mm. The free end of the guide tube may be placed at a distance of between 0 and 100 mm from the MS inlet.

The container 1 and the LTP ionizer 3 may be arranged so that the outlet for the plasma plume P and the surface of the adsorbent membrane when the latter is received therein are spaced apart by 0 to 50 mm. The LTP ionizer may also be arranged to rotate so that the angle formed by the plasma plume and the surface of the adsorbent membrane when the latter is in place is between 3° and 90°, preferably between 35 and 75°, thus making it possible to force the gas towards the MS. The axis of rotation, being horizontal, is perpendicular to the axis of the MS inlet, the angle being acute when the LTP ionizer is remote from the MS. Thus, in this variant of the first embodiment, the plasma plume generated by the LTP ionizer has two functions: desorbing the VOCs and ionizing them.

Figures 6, 7:
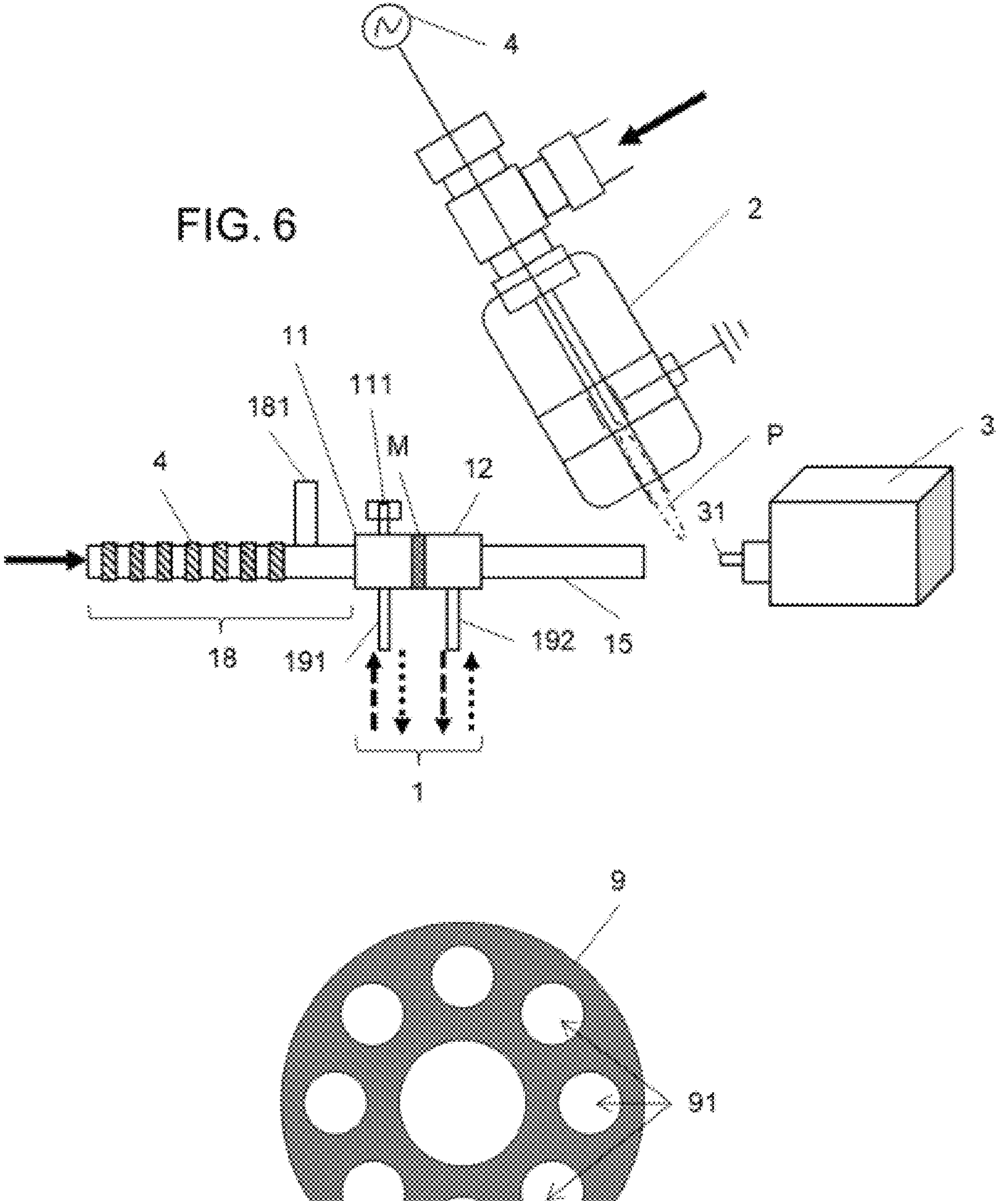
FIG. 6 shows a diagram of a third system where desorption and ionization are carried out remotely.
FIG. 7 shows a diagram of a membrane support in the form of a cylindrical drum, usable in the system of FIG. 6.

As indicated above, FIGS. 4 to 6 show systems in which the receptacle is positioned outside of the plasma stream. A heater (preferably homogeneous) may also be provided for heating the container, in particular between 0 and 500° C., and thus aiding in desorption of the VOCs. Preferably, the heating temperature is between 0 and 400° C., in particular between 20° and 300° C. or even between 225 and 275° C.; for example 50° C., 100° C., 150° C., 200° C., 250° C., 300° C., 350° C., 400° C., 450° C.) and aiding in desorption of the VOCs.

FIGS. 4 to 6 show systems in which the receptacle 1 is a container that is resealable so as to form an enclosed environment except for an inlet and an outlet, and comprises a carrier gas inlet 11 and an outlet 12 for VOC-laden gas.

In these variants, the container 1 may be an Erlenmeyer flask (FIGS. 4 and 5) fitted with a stopper 14, in particular made of cork, with two through-holes made in the stopper 14. The holes allow the insertion of two tubes: a first tube forming a carrier gas inlet 11, its end inserted into the container is close to the bottom of the container; and a second tube forming the outlet 12 for VOC-laden gas, its end inserted into the container is positioned higher than the end of the tube forming the carrier gas inlet. Each of the first and second tubes may have an inside diameter of between 2 and 10 mm.

The carrier gas inlet 11 can be connected to a carrier gas source. In particular, the carrier gas is an inert gas, for example dinitrogen, helium, argon, or a mixture thereof. The gas source may be configured to deliver a flow rate of between 0.5 and 7 L/min. The gas source may be the same as the one for the MS; above 7 L/min, there is a risk of disrupting the plasma.

The heater 4 may be arranged under the receptacle.

More particularly, FIG. 4 shows a system which further comprises a guide tube 15. In this system, the outlet 12 for VOC-laden gas is extended by the guide tube 15, the free end of the tube being close to the plasma stream P, and in particular to the end of the plasma plume, when it is emitted, such that the plasma ionizes the laden gas at the outlet of the guide tube 15 and before it enters the MS 3. The axis of the guide tube 15 preferably forms an angle γ with the upright position, of between 1° and 65°. The distance between the free end of the guide tube 15 and the inlet 31 of the MS may be between 2 and 50 mm. The guide tube 15 may have an inside diameter of between 2 and 10 mm. Furthermore, the guide tube 15 and the second tube forming the outlet 12 for VOC-laden gas may be provided as a single piece.

The LTP ionizer 2 may also be arranged to rotate so that the angle formed by the plasma plume P and the horizontal is between 0 and 90°, preferably between 35 and 75°, thus making it possible to force the gas towards the MS. The axis of rotation, being horizontal, is perpendicular to the axis of the inlet 31 of the MS, the angle being acute when the LTP ionizer 2 is remote from the MS 3. In this case, the LTP ionizer 2 and the MS 3 may be arranged so that the axis of the plasma plume P is coaxial with the inlet 31 of the MS when the angle is equal to 0. In this position with a zero angle, the distance between the end of the plasma plume and the MS inlet may be between 1 and 70 mm.

FIG. 5 shows a system further comprising a two-arm connector 17. A first arm is connected to the outlet 12 of the container 1, for example by means of a hose 16. A second arm has one end oriented towards the inlet 31 of the MS. Although not necessary, preferably the axis of the second arm is coaxial with the inlet 31 of the MS. An orifice placed between the first and second arm is used to receive the plasma plume. This orifice may be replaced by a third arm; the connector is then a three-arm connector.

The three-arm connector 17 may be a T-connector with the first arm and second arm being coaxial along a same first direction and the third arm transverse to the coaxial arms and extending in a second direction different from the first direction.

The inside diameter of the first and second arms may be between 2 and 10 mm. The length between the free ends of the first and second arms may be between 2 and 20 cm. The distance between the MS inlet and the free end of the arm facing it may be between 0 and 70 mm. The length of the hose may be between 2 and 200 cm.

The third arm, or the orifice that replaces it, may be connected to the plasma outlet orifice of the LTP ionizer. This connection may be direct, with the plasma outlet orifice of the LTP ionizer in contact with the third arm or with the edge of the orifice that replaces it, or via a connector (not shown). This connection may be gas-tight or non-gas-tight.

FIG. 6 shows a system which further comprises a carrier gas injection tube 18 and a guide tube 15. The carrier gas injection tube 18 extends along a gas injection axis, and one end thereof, the outlet end, opens into the closed container 1 as the inlet 11 thereof. The closed container is configured to keep the adsorbent membrane M in a position where its surface is perpendicular to the gas injection axis, thereby enabling the carrier gas to become laden with VOCs as it passes through the membrane; for example by comprising a membrane support. The guide tube 15 is used to convey the VOC-laden gas from the outlet 12 of the closed container to the LTP ionizer 2 and the MS 3.

The length of the carrier gas injection tube 18 may be between 5 and 100 cm. The inside diameter of the carrier gas injection tube may be between 2 and 10 mm.

A carrier gas source may be provided and connected to the free end of the gas injection tube, for the injection of inert gas. The inert gas may be nitrogen, water vapor, or a noble gas. In the case where the inert gas is a noble gas, this noble gas may be argon or helium. A mixture of these mentioned gases is also possible. The gas source may be configured to allow a flow rate of carrier gas of between 0.05 and 7 L/min.

The gas source may be the same as that of the MS; above 7 L/min, there is a risk of disrupting the plasma.

The carrier gas injection tube 18 may be fitted with a pressure relief valve 181 and/or the inlet 11 of the closed container with a control valve 111. The pressure relief valve 181 makes it possible to avoid excessive pressure inside the carrier gas injection tube 18, which could damage the adsorbent membrane. The control valve 111 allows controlling the gas flow, in particular with a finer control than that of the inert gas source.

The axis of the guide tube 15 is preferably coaxial with the axis of the MS inlet 31. The length of the guide tube may be between 1 and 10 cm. The inside diameter of the guide tube may be between 1 and 10 mm.

The guide tube 15 may be a three-arm connector with two arms forming the actual guide tube (the first arm being at the outlet of the container 1 and the second arm leading close to or connected to the MS inlet 31) and a third arm for the plasma plume generated by the LTP ionizer 2 to perform ionization in a sealed environment. The three-arm connector may be a T-connector with the first and second coaxial arms forming the actual guide tube and the third arm transverse to the first and second arms. The three-arm connector may be a T-connector with the first and second arms coaxial and the third arm transverse to the first and second arms. The third arm may be connected to the plasma outlet orifice of the LTP ionizer. This connection may be direct, with the plasma outlet orifice of the LTP ionizer in contact with the third arm, or via a connector (not shown). This connection may be gas-tight or non-gas-tight. As with the variant of FIG. 5, the third arm may be replaced by a simple orifice.

In this variant, heating 4 may be provided around the injection tube 18 to heat the carrier gas, for example by means of an electrical heating tape wrapped around the carrier gas injection tube. The electrical heating tape may for example be clamped to the carrier gas injection tube or glued to it.

The closed container 1 may further comprise a sampling inlet 191 for the entry of a sample gas and for loading the adsorbent membrane M with VOCs, and a sampling outlet 192 for the exit of the sample gas. It is thus possible, using a single component, to achieve both the loading of the membrane with a gaseous sample possibly comprising VOCs and the analysis, with no need to manipulate the adsorbent membrane.

For example, the sampling inlet 191 and outlet 192 may be positioned one on either side of the membrane support, along the direction of flow of the carrier gas. Two versions may be provided:

- the sample inlet 191 is downstream and the sample outlet 192 is upstream relative to the direction of flow of the carrier gas (membrane not allowing VOCs to pass through);
- the sample inlet 191 is upstream and the sample outlet 192 is downstream relative to the direction of flow of the carrier gas (membrane allowing VOCs to pass through).

In order to simplify the container, two ports may be provided, one on either side of the membrane support and acting as both inlet and outlet for the sample gas depending on whether the flow of sample gas is in the same direction as the flow of carrier gas or in the opposite direction.

The membrane support 9 may be used as a membrane magazine. In this case, the membrane support 9 may be adapted for insertion by sliding it into a receiving housing. Also, it may be configured to be movable, for example in rotation and/or translation, and comprise a plurality of membrane housing compartments 91. The membrane support 9 may be mounted so as to place a single housing compartment 91, the housing compartment under analysis, between the inlet 11 and the outlet 12 of the closed container 1. Similarly, the membrane support 9 may be mounted so as to place a single housing compartment 91, the loaded housing compartment, between the sampling input 191 and the sampling output 192. The housing compartments 91 are preferably through-holes in which the side wall is a straight cylinder, preferably with a circular base. The membrane support 9 may comprise 2, 3, 4, 5, 6, 7, 8, 9, 10, 11, 12, or even more housing compartments. These housing compartments 91 are preferably regularly distributed on the membrane support 9.

For example, the membrane support 9 may be a rotating drum (FIG. 7) with a plurality of membrane housing compartments 91 distributed angularly around the axis of rotation of the cylinder which is preferably colinear with the flow of carrier gas entering the container 1. These housing compartments 91 are preferably angularly distributed regularly and their center is placed in a same circle for which the center is the axis of rotation of the cylinder. The drum is for example a cylinder with a circular base having the housing compartments and being wider than it is high. The mid-plane of the drum, passing heightwise through its middle, is perpendicular to the flow of carrier gas entering the container 1 such that preferably its axis of rotation is perpendicular to its mid-plane.

Figure 8:
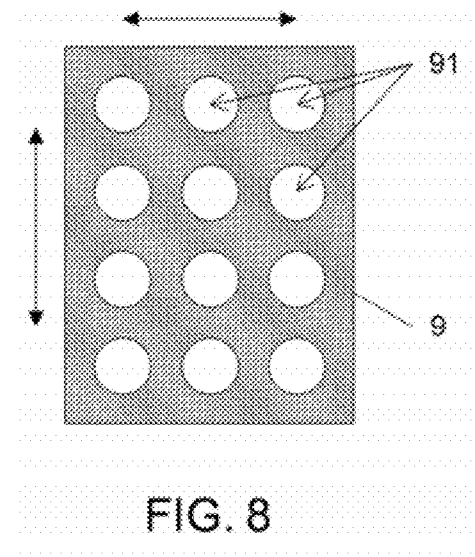
FIG. 8 shows a diagram of a membrane support in the shape of a translational plate usable in the system of FIG. 6.

Alternatively, the membrane support 9 may be a translational plate (FIG. 8) with a plurality of membrane housing compartments 91. The mid-plane (through the thickness) of the translational plate is perpendicular to the flow of carrier gas entering the container 1. The translational plate is mounted to be movable in translation, enabling translational movement in its mid-plane along a single axis or two perpendicular axes. The housing compartments are preferably regularly distributed over the translational plate. The example illustrated in FIG. 8 is particularly suitable for translational movement on two perpendicular axes. A translational plate with membrane housing compartments 91 aligned in a row is particularly suitable for translational movement along a single axis.

Advantageously, the membrane support 9 is made of a material resistant to high temperatures, up to 300° C. in particular, for example stainless steel. The material is preferably also resistant to high pressure, in particular up to 7 bar.

The connections between the membrane support 9 and the components for carrier gas injection or sample loading and unloading are advantageously gas-tight. In order to ensure this gas-tightness, a casing may be provided in which the membrane support 9 is mounted (in particular movable in rotation or in translation). The gas inlet and outlet and/or the sampling inlet and outlet are created in this casing.

The system may comprise an electronic control configured to control the movement of the membrane support 9. The control may also control the loading of a membrane with gaseous sample and/or may control the injection of the carrier gas.

The LTP ionizer 1 may also be arranged to rotate so that the angle formed by the plasma plume and the axis of the guide tube is between 3° and 90°, preferably between 35 and 75°, thus allowing the gas to be forced towards the MS. The axis of rotation, being horizontal, is perpendicular to the axis of the MS inlet, the angle being acute when the LTP ionizer is remote from the MS.

In all cases described above, the source of carrier gases may be that of the MS.

The system may be used in particular with adsorbent membranes which may or may not be in pass-through mode. In other words, during desorption, the VOCs may or may not pass through the adsorbent membrane.

Figure 11:
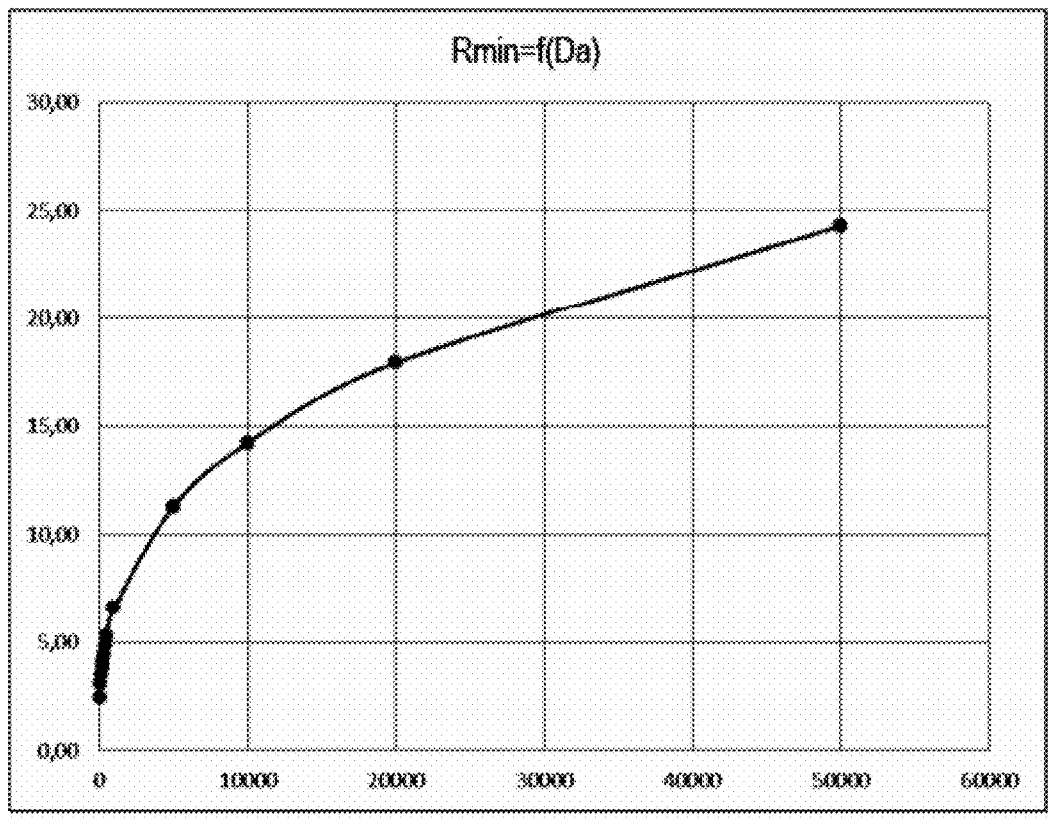

Simulations were carried out to determine the minimum pore size (radius Rmin in ångströms) of an adequate adsorbent membrane, as a function of the size (weight M in daltons) of the VOC molecule in gaseous form and treated as a sphere (see FIG. 11). The graph in FIG. 1 is obtained from known calculations for the size of the compound in spherical form:

$$Rmin = \sqrt[3]{\frac{3}{3300\pi} M} \quad \text{[Math. 1]}$$

The following table gives some points of the graph of FIG. 11.

TABLE 1

| M (Da) | Rmin (Å) |
|---|---|
| 50 | 2.43 |
| 100 | 3.06 |
| 150 | 3.51 |
| 200 | 3.86 |
| 225 | 4.01 |
| 250 | 4.16 |
| 300 | 4.42 |
| 400 | 4.86 |
| 500 | 5.24 |
| 1000 | 6.60 |
| 5000 | 11.29 |
| 10000 | 14.22 |
| 20000 | 17.92 |
| 50000 | 24.31 |

Thus, in order to allow a molecule of 400 Da for example to desorb through the membrane, the pore size must be at least 4.86 Å. The size of the pores of the adsorbent membranes thus determines whether or not they can be used in pass-through mode.

The membranes may be of the carbon-based type, in particular molecular sieves or graphitized carbon black. The membranes may also be of the porous polymer type, in particular polymer based on divinylbenzene or phenyl phenylene oxide or polydimethylsiloxane. The table below summarizes the characteristics of some types of membranes:

TABLE 2

| Type | Material | Specific surface area ($m^2/g$) | Polarity |
|---|---|---|---|
| Carbon | Carbon molecular sieve | 387-485 | Polar |
| | Graphitized carbon black | 240-250 | Nonpolar |
| Porous polymer | Divinylbenzene | 550 | Polar |
| | Phenyl phenylene oxide | 20-35 | Bipolar |
| | PDMS | 280-350 | Nonpolar |

Method

A method for analyzing VOCs adsorbed on an adsorbent membrane and using the system presented above, is described below with reference to FIGS. 1 to 8.

This method comprises providing an adsorbent membrane on which VOCs have been adsorbed, desorbing the VOCs adsorbed on the adsorbent membrane, low-temperature plasma ionizing the desorbed VOCs thereby forming an ionized gas, and analyzing the ionized gas through mass spectrometry.

LTP ionizing typically involves injecting an inert gas into a dielectric barrier discharge, where the inert gas is charged. The inert gas may be nitrogen, water vapor, or a noble gas. In the case of a noble gas, this noble gas may be argon, helium, or neon. A mixture of these mentioned gases is also possible. The injection may be performed at a flow rate of between 50 and 1000 mL/min.

Discharge may be carried out at a voltage of between 1 and 30 kV and/or at a frequency of between 0.8 and 30 kHz. Discharge may be continuous or in pulses.

The method may further comprise heating the adsorbent membrane, in particular to a temperature of between 0 and 400° C.

The method may further include adsorbing the VOCs on the adsorbent membrane.

Adsorbing may comprise preconcentrating the VOCs on the adsorbent membrane. Preconcentrating may be achieved by static headspace sampling (SHS), dynamic headspace sampling (DHS), or solid-phase microextraction (SPME).

When preconcentrating is carried out by static headspace sampling, it may be carried out by aspiration (aspiration dynamic headspace sampling, DHSa) or by sweep gas (sweep gas dynamic headspace sampling, DHSs).

Alternatively, adsorbing may be achieved by placing the adsorbent membrane in front of a potential source of VOCs; for example by placing the adsorbent membrane directly on the skin of a patient, or by directing a patient's breath towards the adsorbent membrane, etc.

Analyzing may include comparing the obtained spectrum/spectra with a database of molecular fingerprints. Each of these molecular fingerprints is a comprehensive VOC spectrum corresponding to given situations (classes), e.g. a healthy person, cancer, cancer type and sub-type, cancer stage, etc. The molecular fingerprints of the database with their class are used to construct classification models with multivariate statistics analysis tools, for example algorithms such as support vector machine (SVM) or latent Dirichlet allocation (LDA), or even by neural networks such as the convolutional neural network (CNN).

Thus, the obtained spectrum/spectra are not compared to isolated spectra of VOCs, but rather the overall appearance of the obtained spectrum/spectra is compared to the appearance of molecular fingerprints in the database. Examples of such comparisons are given below. Alternatively, the obtained spectra may be compared to isolated spectra of VOCs.

Two modes of implementation are possible. In a first mode (corresponding to the systems of FIGS. 1 to 3), ionization is carried out in the immediate vicinity of where desorption takes place, in particular by forming a plasma stream directed towards the adsorbent membrane. In a second mode (corresponding to the systems of FIGS. 4 to 6), ionization is carried out remotely from where desorption takes place.

In the first mode, ionization can be achieved by the formation of a plasma stream directed towards the adsorbent membrane. The plasma stream may be perpendicular to the upper surface of the adsorbent membrane or tilted so that the tip of the plasma plume is oriented towards the MS inlet, by rotating the LPD for example. The tip of the plasma plume may be just flush with or touching the upper surface of the adsorbent membrane.

In a first variant of the first mode (corresponding to the system of FIG. 1), ionization may be carried out at a distance of between 0 and 20 mm from the MS inlet. Ionization may be carried out with an angle of the plasma plume relative to the surface of the adsorbent membrane of between 0 and 90°, the angle being acute when the plasma plume has its tip pointing towards the MS. Desorption and ionization are thus carried out concomitantly by LTP.

In a sub-variant (corresponding to the system of FIG. 2), the method further comprises injecting carrier gas perpendicularly to the lower surface of the adsorbent membrane. The carrier gas may in particular be an inert gas, for example dinitrogen, helium, argon, or a mixture thereof. The flow rate of the carrier gas may be between 0.5 and 7 L/min. Preferably, the carrier gas is injected over the entire lower surface of the adsorbent membrane. Heating of the adsorbent membrane may be achieved by heating the carrier gas before it reaches the lower surface of the adsorbent membrane.

In a second variant of the first mode (corresponding to the system of FIG. 3), desorption and ionization are carried out in a sealed environment except for a gas inlet and outlet as well as a plasma inlet. The adsorbent membrane is placed inside the sealed environment. The method then also comprises injecting a carrier gas into the sealed environment. The injection angle of the carrier gas relative to the surface of the adsorbent membrane may be from 30 to 75°. Injecting the carrier gas may be carried out at a flow rate of 0.5 to 7 L/min. The carrier gas may in particular be an inert gas, for example dinitrogen, helium, argon, or a mixture thereof. Inside the sealed environment, the carrier gas eventually becomes laden with VOCs if VOCs are adsorbed on the adsorbent membrane, and the VOC-laden gas is expelled through the gas outlet towards the MS.

The method may comprise guiding the carrier gas towards the MS inlet such that the direction of flow of the laden gas is coaxial with the MS inlet.

Forming the plasma plume may be carried out so that the axis of the plasma plume and the surface of the adsorbent membrane, when the latter is in place, is between 3° and 90°.

In a first variant of the second mode (corresponding to FIGS. 4 and 5), desorbing is carried out in a sealed environment except for a gas inlet and outlet. The adsorbent membrane is placed in the sealed environment. The method then comprises injecting a carrier gas into the sealed environment. This carrier gas carries away the desorbed VOCs possibly present on the adsorbent membrane, thus forming a VOC-laden gas which leaves the sealed environment through the outlet.

The carrier gas being in particular an inert gas, for example dinitrogen or a noble gas such as helium and argon, or a mixture thereof. The injection of carrier gas may be carried out at a flow rate of between 0.5 and 7 L/min.

Heating may be achieved by heating the receptacle.

More particularly, in a first sub-variant (corresponding to the system of FIG. 4), the VOC-laden gas is guided to the vicinity of the plasma stream, and in particular to the end of the plasma plume, when the stream is emitted, such that the plasma ionizes the laden gas just before it enters into the MS, for example between 2 and 50 mm before the MS inlet. Ionizing thus takes place in the open air. Preferably, guiding the VOC-laden gas is carried out at an angle of between 1° and 65° relative to the vertical.

Ionizing may be carried out so that the plasma plume forms an angle of between 0 and 90° with the horizontal, the angle being acute when the plasma plume is directed towards the MS. It is therefore possible to orient the plasma plume so that it is coaxial with the MS inlet. In this position with an angle of zero, the distance between the end of the plasma plume and the MS inlet may be between 1 and 70 mm.

In a second sub-variant (corresponding to the system in FIG. 5), the VOC-laden gas is guided to the vicinity of the plasma stream, and ionizing is carried out in a sealed environment before exiting the sealed environment towards the MS inlet.

In a second variant (corresponding to the system of FIG. 6), the injection of carrier gas is carried out perpendicularly to the surface of the adsorbent membrane and the guiding of the VOC-laden gas is carried out coaxially with the injection of the carrier gas. The carrier gas is an inert gas, for example nitrogen, water vapor, or a noble gas. In the case where the inert gas is a noble gas, this noble gas may be argon or helium. A mixture of these mentioned gases is also possible. The carrier gas is injected with a carrier gas flow rate of between 0.5 and 7 L/min. Ionization of the VOC-laden gas is carried out either in the open air or in a sealed environment.

In this case, heating is achieved by heating the carrier gas during its injection.

Still in this variant, the method may include loading the adsorbent membrane with gaseous sample when the membrane is already in the closed container and before injecting the carrier gas, which makes it possible to avoid excessive manipulation of the membrane, thus reducing contamination and loss of VOCs. Loading may be carried out in hot conditions or at room temperature. The loading temperature may in particular be lower than the heating temperature. This is particularly advantageous for the adsorbent membranes used in non-pass-through mode although it may also be used for pass-through mode. Alternatively, the membrane may already be laden with VOCs when it is placed in the closed container. Then there is no need to load it with gaseous sample.

Moreover, in this variant, it is possible to carry out the analysis of several samples continuously. To do so, the method further comprises changing the adsorbent membrane before further loading the new adsorbent membrane with gaseous sample, and repeating the other steps of the method. Alternatively, a plurality of membranes already laden with VOCs are placed in the closed container. In both cases, only one membrane at a time is presented to the stream of carrier gas.

Other features of the method are deduced directly from the characteristics of the system described above in these multiple variants. Furthermore, in the embodiments comprising the injection of a carrier gas, heating the membrane may be achieved by the introduction of hot carrier gas, in particular between 23 and 100° C., for example approximately 30° C.

The applications of this method are medical in particular. The methods described above may thus be part of a method for diagnostic aid. In such case, the VOCs come from a patient and have been adsorbed on the adsorbent membrane, for example by physical contact with the patient, or by gas transfer (exhalation) for gas samples. For body fluids (e.g. sweat, saliva, urine), the body fluid is first collected in a container, such as a tube. It is then transferred to the adsorbent membrane, in particular by one of the preconcentration techniques described above (SHS or DHS). Solid samples can be transferred to an adsorbent membrane by solid phase microextraction.

Such a method for diagnostic aid further comprises steps of the method for VOC analysis, the patient's medical status being determined based on the results of the comparison.

This determination is not a diagnosis, which only the doctor is authorized to make, but rather provides an indication to assist the doctor in making decisions. This method for diagnostic aid may advantageously be used for cancer for example, and in particular for breast cancer.

For this purpose, the medical status of the patient provided by the method may include information concerning at least one among the stage, the grade, and the type of cancer the patient is suffering.

Conventionally, a diagnosis is made in order to know the cancer stage, i.e. its extent. For this purpose, doctors use three criteria: i) size and infiltration of the tumor, ii) whether or not the lymph nodes have been affected, and iii) whether or not there are metastases. These criteria are the object of the "TNM" classification (for "Tumor, Nodes, Metastasis") of the Union for International Cancer Control (UICC) and the American Joint Committee on Cancer (AJCC). T relates to tumor size, N to lymph node involvement, and M to distant metastatic spread. For each of these criteria T, N, or M, an annotation is made either as a letter ("x" when the criterion cannot be evaluated, for example when the obtained information is insufficient) or as numbers (from 1 to 4 for T; 1 to 3 for N; and 0 if there is no distant metastasis or 1 if there is). These criteria are evaluated during a clinical examination that can be carried out prior to any treatment in order to know the pre-treatment stage (cTNM classification, c for clinical), or after surgery to know the anatomopathological stage (pTNM classification, p for post-surgical).

Thus, when the patient's medical status includes information about the stage of the cancer, this information includes an annotation for at least one of the T, N and M criteria, preferably all three criteria. This information then statistically indicates to which stage the obtained molecular spectrum corresponds.

Moreover, for breast cancer in particular, not all of the cancers are equally aggressive. Only histological examination can determine this. Conventionally, to do so the practitioner carefully observes tissues taken from the patient, first with the naked eye and then under the microscope. This examination makes it possible to define the grade of the tumor, i.e. its aggressiveness. For this, three criteria are evaluated on a scale ranging from 1 to 3: i) the architecture, 1 indicating that the tumor contains many well-formed structures, 3 that the tumor contains few or no well-formed structures; ii) the nucleus, 1 indicating that the nuclei of the tumor are small and uniform, 3 that the nuclei are large and vary in size and shape; and iii) mitotic activity, 1 indicating slowly dividing tumor cells (low number of mitoses), and 3 indicating rapidly dividing cells (high number of mitoses). The scores given to each of these criteria are then added together and an overall score is obtained. This overall score is classified from I to III which corresponds to the Elston-Ellis histologic grade. If the sum of the scores is 3, 4 or 5, the grade is I (least aggressive tumors); if the sum of the scores is 8 or 9, the grade is III (the most aggressive tumors); if the sum is 6 or 7, the grade is II.

Thus, when the patient's medical status includes information about the grade of the cancer, this information includes an indication of the grade I, II, or III of the cancer; additionally or alternatively, the overall score, ranging from 3 to 9. This information then statistically indicates to which grade the obtained molecular spectrum corresponds.

The optimal treatment for breast cancer depends in particular on the type and subtype of the cancer the patient is suffering. The type relates to the affected region of the breast while the subtype relates to the mutation that is the root cause of the tumor. For example, the breast cancer types are: ductal carcinoma in situ (DCIS), invasive ductal carcinoma (IDC), lobular carcinoma in situ (LCIS), invasive lobular carcinoma (ILC), and inflammatory breast cancer. For example, the breast cancer subtypes are: hormone receptor positive (HR+, relating to estrogen receptors (ER+) and progesterone receptors (PR+)), HER2-positive (HER2+), triple-negative (ER−, PR− and HER2−), and BRCA. It is possible to have a combination of these subtypes.

Thus, when the patient's medical status includes information on the type of cancer, this information includes an indication of the type (for example for breast cancer: DCIS, IDC, LCIS, ILC, or inflammatory) and/or of the subtype (for example for breast cancer: HR+/−, alternatively ER+/− and/or PR+/−; HER2+/−; triple negative, BRCA). This information then statistically indicates to which type and/or subtype the obtained molecular spectrum corresponds.

Figure 12:
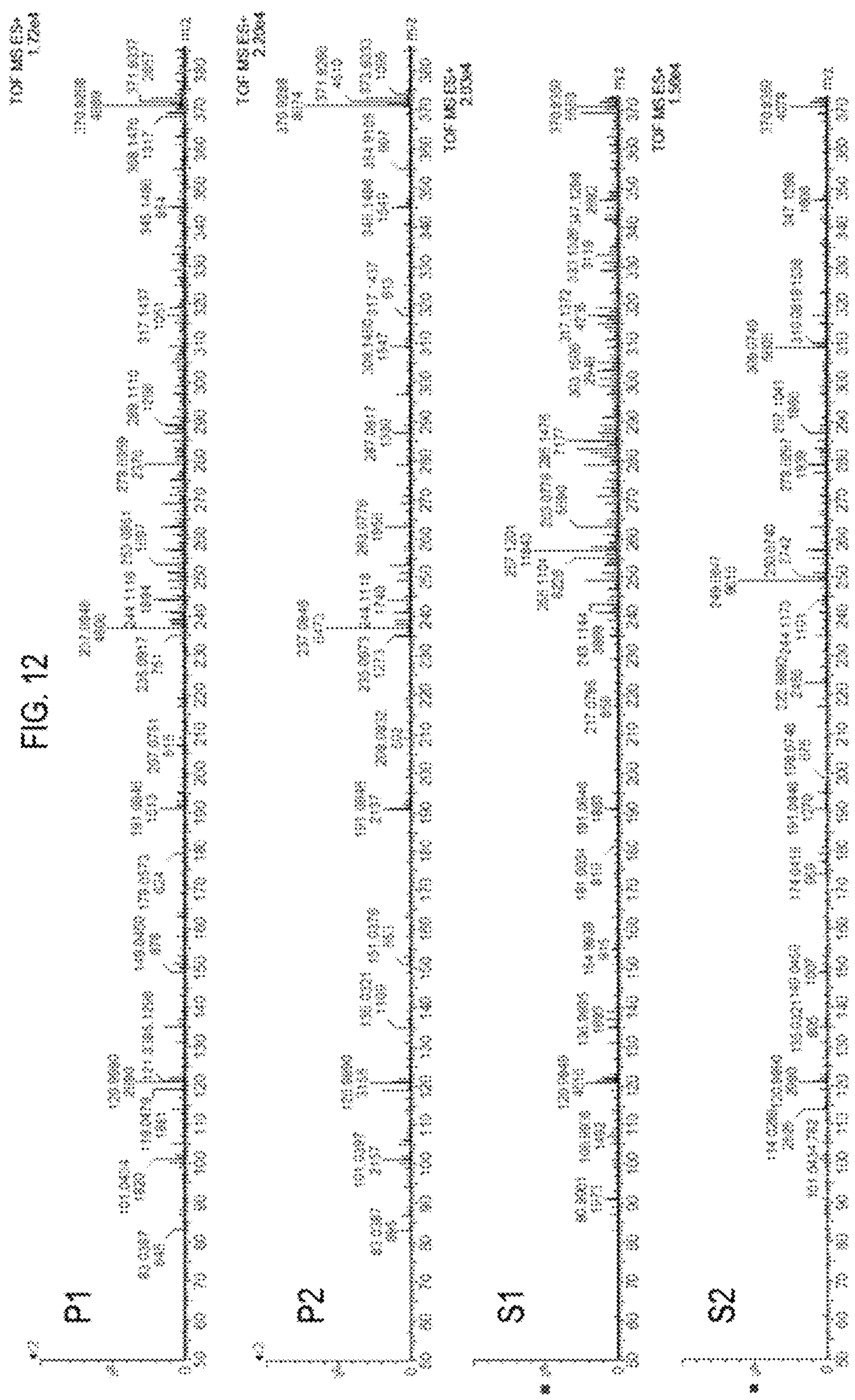
FIG. 12 shows four spectra obtained using the method and system according to the invention: P1 and P2 are spectra obtained from two patients with breast cancer and S1 and S2 are spectra obtained from two healthy people corresponding to the left breast.

FIG. 12 shows examples of obtained spectra providing the molecular signature of samples. The spectra obtained for four samples from four people are shown in this figure: two patients with breast cancer and two healthy people. The samples are obtained by placing an adsorbent membrane directly on the chest of these individuals. P1 is a patient with breast cancer in the metastatic stage with involvement of bones and the right breast; her profile is HR+ and HER2−. P2 is a patient with early stage breast cancer with involvement of the left breast and the underlying lymph nodes; her profile is HR+ and HER2−. S1 and S2 are two healthy individuals, i.e. not suffering from breast cancer. Spectra S1 and S2 can serve as controls.

As is conventional, the abscissa represents the mass-to-charge ratio (m/z) of the fragments detected. The four spectra are aligned with each other on this axis. The numbers given indicate the m/z ratio at the top and the height of the peak at the bottom.

It is clear from the four spectra that those relating to the patients have a similar general appearance and that those relating to the healthy individuals also have a similar general appearance. In addition, the spectra of the patients have a different appearance than those of the healthy individuals. In particular, the two spectra of the patients include the following peaks (m/z): 83.04; 101.04; 237.09; 345.15. The spectrum of patient P1 also has a peak at 119.05, and that of patient P2 has a peak at 309.13. These peaks are not present in the spectra of the healthy individuals.

Thus, it is not so much the peak corresponding to a particular compound that is of interest, but rather the general appearance of the spectrum obtained.

Moreover, two spectra obtained from adsorbent membranes placed in contact with the skin of a patient, on an affected breast for one and on a healthy breast for the other, do not have an identical appearance.

Figure 13:
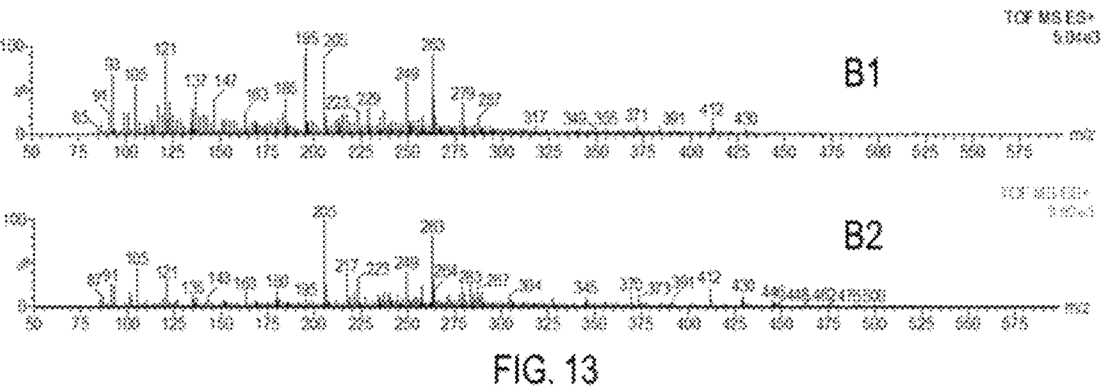
FIG. 13 shows two spectra obtained from a same patient using the method and system according to the invention: B1 is the spectrum corresponding to the right breast and B2 to the left breast.

Indeed, FIG. 13 shows two spectra obtained from two adsorbent membranes placed on the skin of a same patient. B1 corresponds to the right breast and B2 corresponds to the left breast. The right breast is the breast with a tumor while the left breast has no tumor. These spectra are almost identical with the notable difference that the spectrum for the right breast includes a peak at m/z=195 while the spectrum for the left breast does not. Thus, in addition to enabling detection of an affected person, it is also possible to know the organ affected.

Other applications may be envisaged, however, such as olfactory analysis of beverages (beer and wine) or other food products, or analysis of hydrocarbons.

EXAMPLES

Example 1 of the system for analyzing VOCs adsorbed on an adsorbent membrane, by LTP-MS, comprises:

a receptacle for receiving the adsorbent membrane;

a low-temperature plasma ionizer suitable for emitting a plasma stream in a plasma emission direction, thus ionizing the VOCs adsorbed by the membrane and forming an ionized gas laden with VOCs; and a mass spectrometer for analyzing the ionized VOCs.

Example 2 of the system comprises the elements of Example 1 and, in addition, a heater for heating the adsorbent membrane.

Example 3 of the system comprises the elements of Example 1 or Example 2. In addition, in Example 3 the receptacle is placed outside of the plasma stream.

Example 4 of the system comprises the elements of Example 3. In addition, in Example 4:

the receptacle is a container that is resealable so as to form a sealed environment except for an inlet and an outlet;

the container comprises a carrier gas inlet for the entry of a carrier gas into the container and a gas outlet for the exit of a gas potentially laden with VOCs.

Example 5 of the system comprises the elements of Example 4. In addition, Example 5 comprises:

a carrier gas injection tube extending along a gas injection axis and of which one of the ends, the outlet end, opens into the closed container, the closed container being configured to keep the adsorbent membrane so that its surface is perpendicular to the gas injection axis, thus allowing the carrier gas to become laden with VOCs as it passes through the membrane; and a guide tube for conveying the VOC-laden carrier gas to the ionizer.

Example 6 of the system comprises the elements of Example 5. In addition, Example 6 comprises the heater which is arranged around the injection tube in order to heat the carrier gas.

Example 7 of the system comprises the elements of Example 5 or Example 6. In Example 7, the closed container comprises a membrane support for supporting a membrane, a sampling inlet for the entry of a sample gas and the loading of the membrane with VOCs, a sampling outlet for the exit of the sample gas, a carrier gas inlet.

Example 8 comprises the elements of Example 7. In Example 8, the membrane support is a membrane magazine configured to be moved in rotation and/or translation and comprises a plurality of membrane housings, the membrane magazine being mounted so as to place a single housing, the housing under analysis, opposite the outlet end of the injection tube and the inlet end of the guide tube.

Example 9 of the system comprises the elements of Example 7 or Example 8. In Example 9, the membrane magazine is mounted so as to place a single housing, the housing laden with sample, between the sampling inlet and the sampling outlet.

Example 10 of the system comprises the elements of Example 4 and a guide tube. In Example 10:

the container outlet is extended by the guide tube, the free end of the tube being close to the plasma stream when the stream is emitted so that the plasma ionizes the laden gas at the tube outlet.

Example 11 of the system comprises the elements of Example 4, and a three-arm connector. In Example 11:

a first arm is connected to the outlet of the container;

a second arm has one end directed towards the inlet of the mass spectrometer;

the ionizer is configured so that the plasma stream is directed towards the third arm during operation.

Example 12 of the system comprises the elements of Example 1 or Example 2. In Example 12, the receptacle is arranged under the plasma stream such that the plasma stream is directed towards the membrane when the membrane is received in the receptacle.

Example 13 of the system comprises the elements of Example 12. In Example 13:

the receptacle is a container that is resealable so as to form a sealed environment except for inlets and an outlet;

the container comprises a carrier gas inlet for the entry of a carrier gas into the container, a gas outlet for the exit of the ionized gas, and a plasma inlet;

the outlet is extended by a guide tube for guiding the ionized gas towards the inlet of the mass spectrometer.

Example 14 of the system comprises the elements of any of Examples 1 through 13. In Example 14, the ionizer is an ionizer with one electrode or two electrodes.

Example 15 of the system comprises the elements of Example 14. In Example 15, the ionizer is configured for an injection of inert gas at a flow rate of between 50 and 1000 mL/min.

Example 16 of the system comprises the elements of any of Examples 1 to 15, and in addition a power supply for powering the ionizer, in particular at a voltage of between 1 and 30 kV and in particular at a frequency of between 0.8 and 30 kHz.

Example 17 is a method for analyzing VOCs adsorbed on an adsorbent membrane, by LTP-MS, comprising:

providing of an adsorbent membrane on which VOCs have been adsorbed;

desorption of the VOCs adsorbed on the adsorbent membrane;

low-temperature plasma ionization of the desorbed VOCs, thereby forming an ionized gas; and analysis of the ionized gas, by mass spectrometry.

Example 18 of the method comprises the elements of Example 17 and the heating of the membrane.

Example 19 of the method comprises the elements of Example 17 or Example 18. In Example 19, the ionization is performed remotely from the desorption.

Example 20 of the method comprises the elements of Example 21. In Example 20, the desorption is carried out in a sealed environment except for a gas inlet and outlet, the adsorbent membrane being arranged in the sealed environment; the method further comprising the injection of a carrier gas through the gas inlet in order to carry away the desorbed VOCs thereby forming a VOC-laden gas.

Example 21 of the method comprises the elements of Example 20, the injection of a carrier gas perpendicularly to the surface of the adsorbent membrane, and the guiding of the VOC-laden gas from injection of the carrier gas until ionization.

Example 22 of the method comprises the elements of Example 21 and the heating of the carrier gas during its injection.

Example 23 of the method comprises the elements of Example 20 and the guiding of the VOC-laden gas from the desorption site to the ionization site. In Example 23, the ionization is carried out in the open air.

Example 24 of the method comprises the elements of Example 20 and the guiding of the VOC-laden gas from the desorption site to the ionization site. In Example 24, the ionization is carried out in a sealed environment.

Example 25 of the method comprises the elements of Example 17 or Example 18. In Example 25, the ionization is carried out in close proximity to the desorption, in particular by formation of a plasma stream directed towards the adsorbent membrane.

Example 26 of the method comprises the elements of Example 25. In Example 26, the desorption and ionization are carried out in a sealed environment except for a gas inlet and outlet and where the adsorbent membrane is located. Example 26 further comprises the injection of a carrier gas through the gas inlet.

Example 27 of the method comprises the elements of any one of examples 17 to 26. In Example 27, the low-temperature plasma generated during ionization is obtained from an inert gas, in particular dinitrogen or a noble gas, for example argon, helium, or neon.

Example 28 of the method comprises the elements of Example 27. In Example 28, the flow rate of the internal gas is between 50 and 1000 mL/min.

Example 29 of the method comprises the elements of any of Examples 17 to 28. In Example 29, the ionization is powered by a voltage source at a voltage of between 1 and 30 kV.

Example 30 of the method comprises the elements of any of Examples 17 to 29. In Example 30, the ionization is powered by an energy source at a frequency of between 0.8 and 30 kHz.

Example 31 of the method comprises the elements of any of Examples 17 to 30, and the adsorption of VOCs on the adsorbent membrane.

Example 32 of the method comprises the elements of Example 31. In Example 32, the adsorption includes preconcentration of the VOCs on the adsorbent membrane.

Example 33 of the method comprises the elements of Example 32. In Example 33, the preconcentration is performed by static headspace sampling, dynamic headspace sampling, or solid-phase microextraction.

Example 34 of the method comprises the elements of Example 33. In Example 34, the preconcentration is performed by static headspace sampling-aspiration or static headspace sampling-sweep gas.

Example 35 of the method comprises the elements of any of Examples 17 to 34. In Example 35, the analysis comprises comparing the obtained spectra to a database of molecular fingerprints.

Example 36 of the method comprises the elements of Example 35. In Example 36, VOCs from the patient have been adsorbed on the adsorbent membrane. Example 36 further comprises the determination of the patient's medical status based on the comparison.

Example 37 of the method comprises the elements of Example 36. In Example 37, the patient's medical status includes information concerning at least one among the stage, grade, and type of cancer affecting the patient.

Example 38 comprises the elements of Example 37. In Example 38, the cancer is breast cancer.

Example 39 comprises the elements of Example 38. In Example 39, the adsorption is carried out by placing the adsorbent membrane in contact with the patient's skin, for adsorption of the VOCs.

Example 40 is a method for diagnostic aid, including the elements of Example 35. In Example 40, VOCs from the patient have been adsorbed on the adsorbent membrane. Example 40 further comprises the determination of the patient's medical status based on the comparison.

Example 41 comprises the elements of Example 40. In Example 41, the patient's medical status includes information concerning at least one among the stage, grade, and type of cancer affecting the patient.

Example 42 comprises the elements of Example 40 or Example 41. In Example 42, the method is a method for diagnostic aid, for the diagnosis of breast cancer.

Example 43 comprises the elements of Example 42. In Example 43, the adsorption is carried out by placing the adsorbent membrane in contact with the patient's skin for adsorption of the VOCs.

The invention claimed is:

1. A system for analyzing volatile organic compounds (VOCs) that have been collected by contact sampling on an adsorbent interface membrane, by low-temperature plasma and mass spectrometry (LTP-MS), comprising:

an adsorbent interface membrane permeable to VOCs, having a first face and a second face, said adsorbent interface membrane configured to ensure controlled diffusion of the VOCs from the first face to the second face:

a receptacle for receiving the adsorbent interface membrane, the receptacle positioning the adsorbent interface membrane such that the first face is contactable with a VOC source for sampling;

a low-temperature plasma ionizer configured to emit a plasma stream in a plasma emission direction, ionizing the VOCs adsorbed by the adsorbent interface membrane to diffuse the VOCs to the second face of the adsorbent interface membrane to form an ionized gas laden with VOCs; and a mass spectrometer configured to analyze the ionized gas laden with VOCs.

2. The system according to claim 1, further comprising a heater for heating the adsorbent interface membrane.

3. The system according to claim 1, wherein the receptacle is positioned outside the plasma stream and wherein:

the receptacle is a container that is resealable so as to form a sealed environment except for an inlet and an outlet;

the container comprises a carrier gas inlet for the entry of a carrier gas into the container and a gas outlet for the exit of a gas potentially laden with VOCs.

4. The system according to claim 3, further comprising:

a carrier gas injection tube extending along a gas injection axis and of which one end, the outlet end, opens into the closed container, the closed container being configured to hold the adsorbent interface membrane so that its surface is perpendicular to the gas injection axis, thereby enabling the carrier gas to become laden with VOCs as it passes through the adsorbent interface membrane; and a guide tube for conveying the VOC-laden carrier gas to the ionizer.

5. The system according to claim 4, wherein the closed container comprises a membrane support for supporting the adsorbent interface membrane, a sampling inlet for the entry of a sample gas and the loading of the adsorbent interface membrane with VOCs, a sampling outlet for the exit of the sample gas, a carrier gas inlet.

6. The system according to claim 5, wherein the membrane support is a membrane magazine configured to be moved in rotation and/or translation and comprising a plurality of membrane housing compartments, the membrane magazine being mounted so as to place a single housing compartment, the housing compartment under analysis, opposite the outlet end of the injection tube and the inlet end of the guide tube.

7. The system according to claim 4, further comprising a guide tube and wherein:

the container outlet is extended by the guide tube, the free end of the tube being close to the plasma stream when said stream is emitted so that the plasma ionizes the laden gas at the tube outlet.

8. The system according to claim 3, further comprising a connector with at least two arms, and wherein:

a first arm is connected to the outlet of the container;

a second arm has one end directed towards the inlet of the mass spectrometer;

the ionizer is configured so that the plasma stream is directed towards an opening between the first and second arm or a third arm during operation.

9. The system according to claim 1, wherein the receptacle is arranged under the plasma stream such that the plasma stream is directed towards the adsorbent interface membrane when the adsorbent interface membrane is received in the receptacle.

10. The system according to claim 9, wherein:

the receptacle is a container that is resealable so as to form a sealed environment except for inlets and an outlet;

the container comprises a carrier gas inlet for the entry of a carrier gas into the container, a gas outlet for the exit of the ionized gas, and a plasma inlet;

the outlet is extended by a guide tube for guiding the ionized gas towards the inlet of the mass spectrometer.

11. The system according to claim 1, wherein the ionizer is an ionizer with one electrode or two electrodes.

12. A method for analyzing VOCs adsorbed on an adsorbent interface membrane, by LTP-MS, using the system according to claim 1, the method comprising:

providing an adsorbent interface membrane on which VOCs have been adsorbed;

desorbing the VOCs adsorbed on the adsorbent membrane;

low-temperature plasma ionizing the desorbed VOCs, thereby forming an ionized gas; and analyzing the ionized gas, by mass spectrometry.

13. The method according to claim 12, wherein analyzing comprises comparing the obtained spectra with a database of molecular fingerprints.

14. The method according to claim 13, wherein VOCs from a patient have been adsorbed on the adsorbent interface membrane, the method further comprising determining the patient's medical status based on the results of the comparison.

15. The method according to claim 14, wherein the patient's medical status includes information concerning at least one among the stage, grade, and type of breast cancer.

16. A method for diagnostic aid, in particular for breast cancer, comprising the method according to claim 13, wherein VOCs from the patient have been adsorbed on the adsorbent interface membrane, the method further comprising determining the patient's medical status based on the results of the comparison.

17. The method according to claim 16, wherein the patient's medical status includes information concerning at least one among the stage, grade, and type of breast cancer.

* * * * *